(12) United States Patent
Weitz et al.

(10) Patent No.: US 10,333,072 B2
(45) Date of Patent: Jun. 25, 2019

(54) THIN FILM SEMICONDUCTOR COMPRISING A SMALL-MOLECULAR SEMICONDUCTING COMPOUND AND A NON-CONDUCTIVE POLYMER

(71) Applicant: BASF SE, Ludwigshafen (DE)

(72) Inventors: Thomas Weitz, Mannheim (DE); Thomas Gessner, Heidelberg (DE); Junichi Takeya, Kashiwa (JP); Masayuki Kishi, Ichikawa (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/506,802

(22) PCT Filed: Aug. 20, 2015

(86) PCT No.: PCT/IB2015/056318
§ 371 (c)(1),
(2) Date: Feb. 27, 2017

(87) PCT Pub. No.: WO2016/030800
PCT Pub. Date: Mar. 3, 2016

(65) Prior Publication Data
US 2017/0244045 A1 Aug. 24, 2017

(30) Foreign Application Priority Data

Aug. 28, 2014 (EP) .................................. 14182710

(51) Int. Cl.
*H01L 51/00* (2006.01)
*C07D 471/00* (2006.01)
(Continued)

(52) U.S. Cl.
CPC ........ *H01L 51/0053* (2013.01); *C07D 471/06* (2013.01); *H01L 51/004* (2013.01); *H01L 51/0566* (2013.01)

(58) Field of Classification Search
USPC ........................................................ 252/500
See application file for complete search history.

(56) References Cited

U.S. PATENT DOCUMENTS

| | | | |
|---|---|---|---|
| 6,215,130 B1 | 4/2001 | Dodabalapur | |
| 6,232,157 B1 | 5/2001 | Dodabalapur et al. | |
| 2006/0099526 A1 | 5/2006 | Yang | |
| 2008/0054257 A1 | 3/2008 | Tsai et al. | |

(Continued)

FOREIGN PATENT DOCUMENTS

EP        0 981 165 A1    2/2000

OTHER PUBLICATIONS

International Search Report dated Nov. 27, 2015 in PCT/IB2015/056318 filed Aug. 20, 2015.

*Primary Examiner* — Harold Y Pyon
*Assistant Examiner* — Danny N Kang
(74) *Attorney, Agent, or Firm* — Oblon, McClelland, Maier & Neustadt, L.L.P.

(57) ABSTRACT

A thin film semiconductor comprising a compound of formula I or II wherein: $R^1$ and $R^2$, at each occurrence, independently are selected from a $C_{1-30}$ alkyl group, a $C_{2-30}$ alkenyl group, a $C_{2-30}$ alkynyl group and a $C_{1-30}$ haloalkyl group, $R^3$, $R^4$, $R^5$, and $R^6$ independently are H or an (Continued)

electron-withdrawing group, wherein at least one of $R^3$, $R^4$, $R^5$, and $R^6$ is an electron-withdrawing group; and a non-conductive polymer.

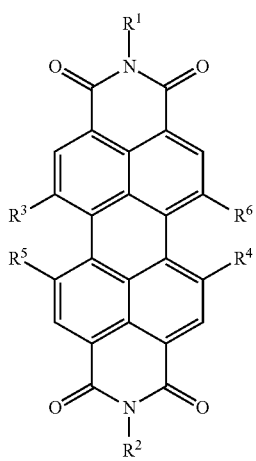

I

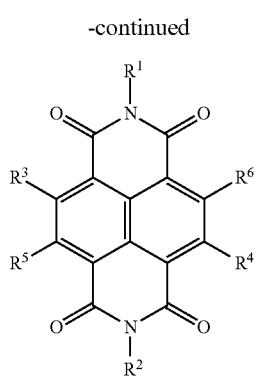

II

9 Claims, 2 Drawing Sheets

(51) Int. Cl.
  *H01L 51/05* (2006.01)
  *C07D 471/06* (2006.01)

(56) References Cited

U.S. PATENT DOCUMENTS

2010/0319778 A1* 12/2010 Kastler ............... C07D 471/06
                                                                    136/263
2012/0199824 A1    8/2012 Ichikawa et al.

* cited by examiner

THIN FILM SEMICONDUCTOR COMPRISING A SMALL-MOLECULAR SEMICONDUCTING COMPOUND AND A NON-CONDUCTIVE POLYMER

The invention relates to a thin film semiconductor comprising a small-molecular semiconducting compound and a non-conductive polymer, to a solution containing the compound, the polymer and a solvent, and to the use of the solution for growing large area crystalline semiconducting thin films.

Organic field-effect transistors (OFETs) are promising candidates for next-generation electronic switches based on low-cost and environmentally friendly semiconductor materials, which are also lightweight and flexible. Solution-processed high-performance field-effect devices are particularly desirable for large-area electronics for new industrial applications, which have not been considered through the use of conventional silicon technologies. Methods such as printing enable simple high-throughput fabrication compared with conventional vacuum processes, which are not cost-effective for large-area devices, because of the huge vacuum chambers that would be necessary. Conventional techniques such as spin coating and drop casting can be easily applied to large-area device fabrication. However, the performance of OFETs based on polymer or soluble small-molecular semiconductors is still not satisfactory; the typical carrier mobility reported for solution-processed OFETs remains on the order of 0.1 cm$^2$ V$^{-1}$ s$^{-1}$. The presence of grain boundaries and the random molecular orientation can hinder charge transport.

To improve the periodicity in the alignment of the molecules, several solution methods have been recently proposed for growing single-crystalline organic semiconductor films (H. Mine-mawari, T. Yamada, H. Matsui, J. Tsutsumi, S. Haas, R. Chiba, R. Kumai, and T. Hasegawa: Nature 475 (2011) 364; J. Soeda, T. Uemura, Y. Mizuno, A. Nakao, Y. Nakazawa, A. Facchetti, and J. Takeya: Adv. Mater. 23 (2011) 3681; G. Giri, E. Verploegen, S. C. B. Mannsfeld, S. Ata-han-Evrenk, D. H. Kim, S. Y. Lee, H. A. Becerril, A. Aspuru-Guzik, M. F. Toney, and Z. Bao: Nature 480 (2011) 504; K. Sakamoto, J. Ueno, K. Bulgarevich, and K. Miki: Appl. Phys. Lett. 100 (2012) 123301). T. Uemura, Y. Hirose, M. Uno, K. Takimiya, and J. Takeya: Appl. Phys. Express 2 (2009) 111501 and K. Nakayama, Y. Hirose, J. Soeda, M. Yoshizumi, T. Uemura, M. Uno, W. Li, M. J. Kang, M. Yamagishi, Y. Okada, E. Miyazaki, Y. Nakazawa, A. Nakao, K. Takimiya, and J. Takeya: Adv. Mater. 23 (2011) 1626 describe a method for creating highly crystalline organic semiconductor films which increases the carrier mobility of solution-processed thin-film transistors (TFTs) by more than one order of magnitude, to 5-10 cm$^2$ V$^{-1}$ s$^{-1}$. The method uses an edge to control the shape of an attached droplet, so that the thickness of the liquid gradually decreases as the distance from the solid edge increases. This method controls the direction of the crystal growth through the asymmetrical evaporation of the solvent, and allows continuous uniform crystalline films to be formed. The edge-cast films are highly crystalline, which results in the exceptionally high mobility. However, crystals prepared by this technique do not grow beyond sub-millimeter sizes, because the process finishes when all the solvent has evaporated. Therefore, the method is not suitable for large-area electronic devices, for which solution processes are usually most appropriate.

J. Soeda, T. Uemura, T. Okamoto, C. Mitsui, M. Yamagishi, and J. Takeya: Inch-Size Solution-Processed Single-Crystalline Films of High-Mobility Organic Semiconductors, Applied Physics, Express 6 (2013) 076503 report a modified edge-casting solution-crystallization technique for producing much larger domain single-crystalline organic semiconductors by controlling the crystal growth direction. A mobile solid blade edge was used to hold an organic semiconductor droplet in a rectangle, so that level-contour lines of the liquid-gas boundary, measured from the horizontal surface of the substrate, were parallel to the edge of the blade. The rectangular droplet was kept the same size by replenishing the organic semiconductor solution at the same rate as the solvent evaporation. As a result, large-domain crystal films were grown continuously to several inches in size. Square crystals greater than 3×2 cm$^2$ in size were obtained and arrays of TFTs were prepared to examine the OFET performance. X-ray diffraction (XRD) measurements were used to determine the crystallinity of the single-crystalline thin films.

It is an object of the present invention to provide large-domain crystalline semiconducting thin films based on soluble small-molecular semiconductors.

The object is solved by a thin film semiconductor comprising a compound of formula I or II

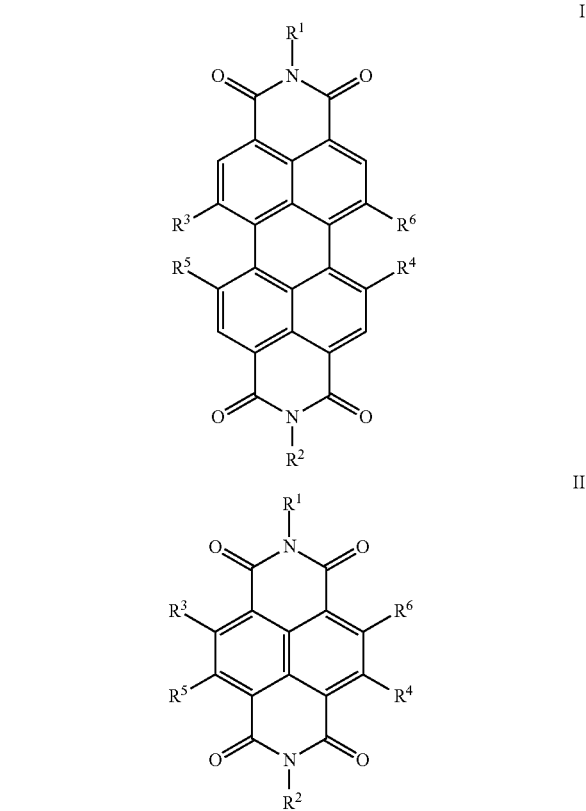

wherein:
R$^1$ and R$^2$, at each occurrence, independently are selected from a C$_{1-30}$ alkyl group, a C$_{2-30}$ alkenyl group, a C$_{2-30}$ alkynyl group and a C$_{1-30}$ haloalkyl group,
R$^3$, R$^4$, R$^5$, and R$^6$ independently are H or an electron-withdrawing group, wherein at least one of R$^3$, R$^4$, R$^5$, and R$^6$ is an electron-withdrawing group; and a non-conductive polymer.

The inventors have found that the drying speed of the solvent can be controlled by mixing a non-conductive polymer with the organic semiconductor solution, thereby stabilizing the growth process of the thin film and improving the crystallinity of the thin film. In a preferred embodiment, poly(methylmethacrylate) (PMMA) was used as the non-conductive polymer. Further suitable non-conductive polymers are e.g. polystyrene and polyethylene terephthalate In a preferred embodiment, $R^1$ and $R^2$ in formula I and II, at each occurrence, are selected from a $C_{1-12}$ alkyl group and a $C_{1-12}$ haloalkyl group.

In general, each of $R^3$, $R^4$, $R^5$, and $R^6$ in formula I and II is selected from H, F, Cl, Br, I, and —CN.

In a first preferred embodiment, each of $R^3$ and $R^4$ in formula I and II is Br or —CN and $R^5$ and $R^6$ are H.

In a second preferred embodiment, each of $R^3$ and $R^6$ in formula I and II is Br or —CN and $R^4$ and $R^5$ are H.

Very preferred are compounds having formula Ia or formula Ib

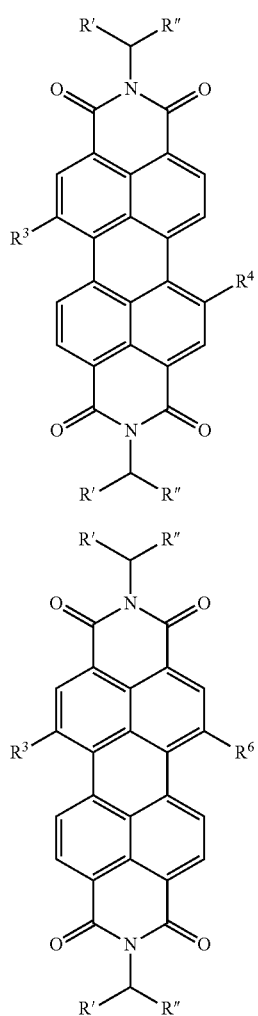

wherein R', R" are, at each occurrence, selected from a $C_{1-12}$ alkyl group and a $C_{1-12}$ haloakyl group, and $R^3$, $R^4$, and $R^6$ are as defined herein above.

An example of a very preferred compound of formula I is

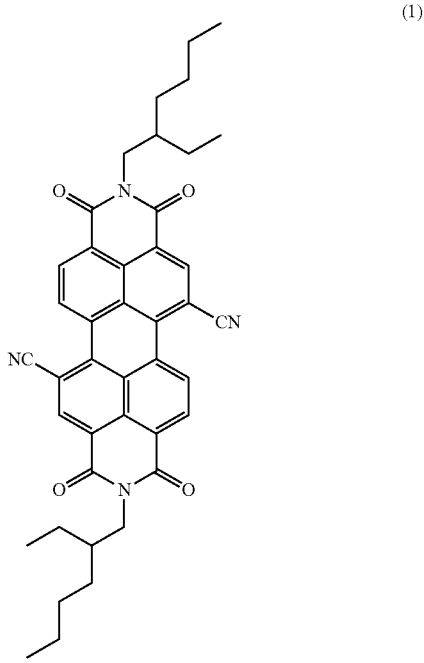 [SMILES: CCCCC(CC)CN1C(=O)c2ccc3c4c(C#N)cc5c6c(ccc(c7c(C#N)cc(c2c37)C1=O)c64)C(=O)N(CC(CC)CCCC)C5=O]

(1)

Examples of very preferred compounds of formula II are

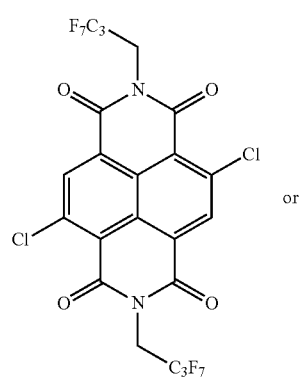

(2)

or

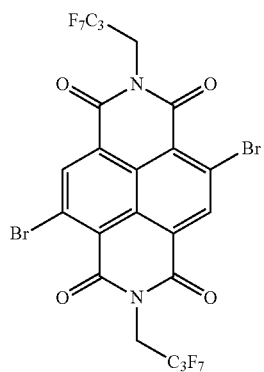

(3)

The present invention also relates to a solution containing a compound of formula I or II, a non-conductive organic polymer and a solvent, as well as to the use of the solution for growing crystalline semiconducting thin films on a substrate.

Any high-boiling organic solvent in which the compounds of formula I and II are sufficiently soluble is suitable. Preferred are high-boiling aromatic hydrocarbons and halogenated aromatic hydrocarbons having a boiling point above 150° C., more preferably above 170° C., such as ortho-dichlorobenzene and tetralin. The non-conductive polymer is preferably poly(methylmethacrylate).

The semiconducting compound of formula I and II and the non-conductive polymer are in general used in concentrations of from 0.1 to 1.0 wt.-% each. The weight ratio of semiconducting compound to non-conductive polymer in the solution and in the semiconducting film is in general form 5:1 to 1:5, preferably from 2:1 to 1:2, for example 1:1.

The semiconducting films are preferably grown with the modified edge-cast method described above. Large-area single-crystalline organic semiconductor thin films are continuously grown through the use of a mobile solution-holding blade. Highly uniform thin films of p- and n-type low molecular weight organic semiconductors, up to 10 cm×10 cm in size, are grown at the edge of the blade. XRD confirmed that the crystallinity of the films was excellent. The arrayed OFET based on the large-domain crystal films exhibited excellent mobilities of 5-10 $cm^2V^{-1} s^{-1}$. The crystal growth method is easy, and can be used for high-throughput large-area printing in low-cost printing fabrication of high-speed organic semiconductor TFTs.

EXAMPLES

Example 1

The semiconductor material, selected from the three example compounds (1)-(3) shown above, was dissolved in typical aromatic solvent such as o-dichlorobenzene (bp=180° C.) or tetralin (bp=206° C.) at a concentration of 0.1 wt.-%. To this solution, 0.1 wt.-% of poly(methylmethacrylate) was added and dissolved.

The glass substrates were treated with a phenyl-substituted silane-based self-assembled mono-layer [trimethoxy (2-phenylethyl)silane, ß-PTS] to increase the wettability of the solution on the substrate. A syringe pump was used to supply the solution containing the semiconductor and the polymer to the edge of the blade on the substrate at a constant rate. The substrate temperature was kept at 80° C., and the gap between the substrate and the blade was 200 µm. The blade was moved slowly in the direction indicated in FIG. 1 at a speed of 30 µm/s to grow the thin-film crystals at the edge of the blade.

Example 2

Figure 1:
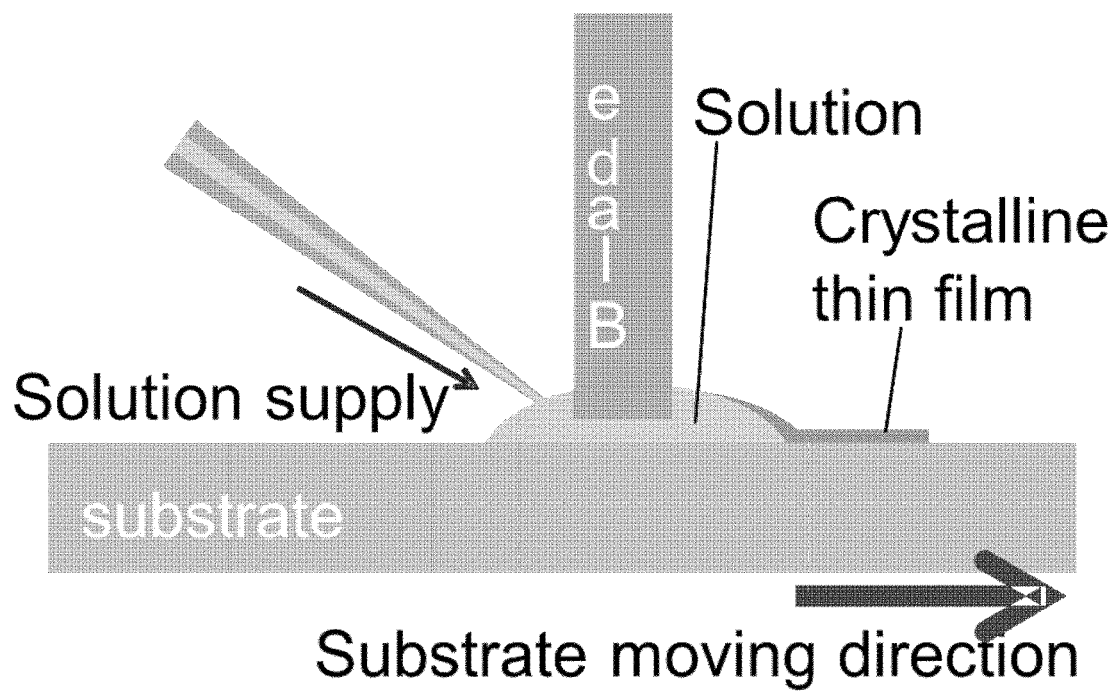
Figure 2:
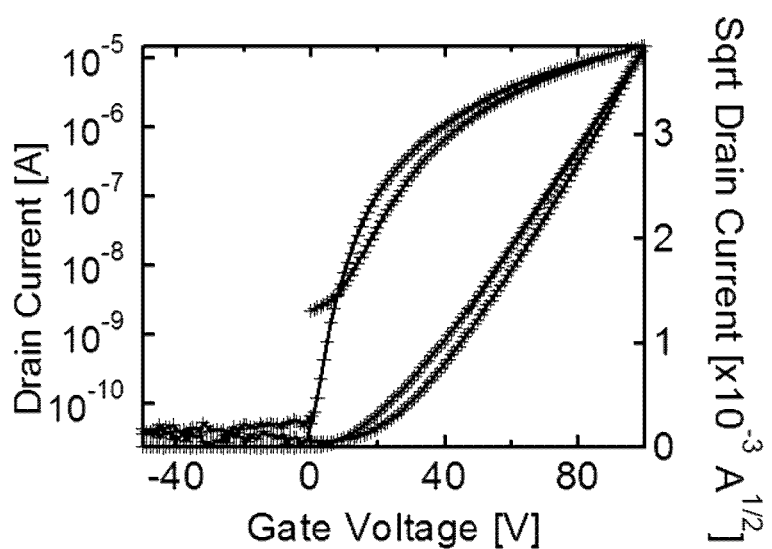
FIG. 2 shows typical transfer characteristics of the n-type solution crystallized TFT containing the semiconducting compound and PMMA.
Figure 3:
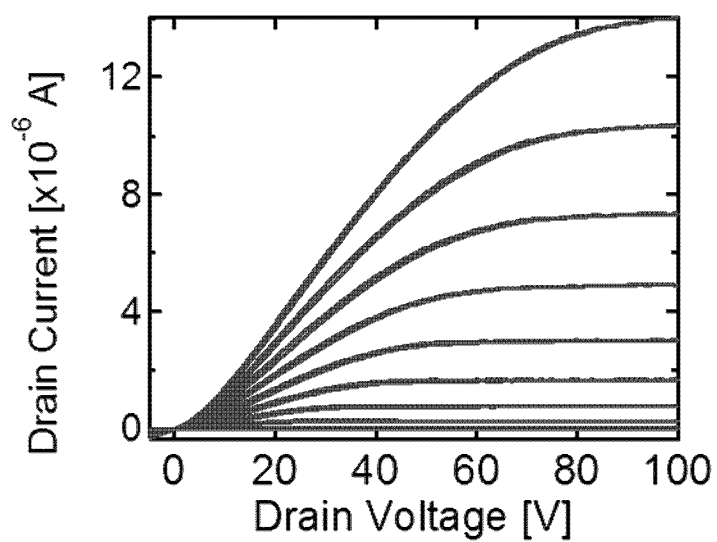
FIG. 3 shows the output characteristics of the n-type solution crystallized TFT containing the semiconducting compound and PMMA.

Example compound (3) was dissolved in anisole at a concentration of 0.15 wt.-%. To this solution, 0.042 wt.-% of poly(methylmethacrylate) was added and dissolved.

From this solution, a BGTC device was produced. The thin-film crystal layer was fabricated on an $SiO_2$ treated with ß-PTS on doped Si by continuous edge-casting as in Example 1 while keeping the solution and substrate temperature at 100° C. The device characterization indicated that the electron mobility is 0.28 $cm^2/Vs$ and the threshold voltage is 4.2 V.

The invention claimed is:
1. A thin film semiconductor comprising a compound of the following formula I or II:

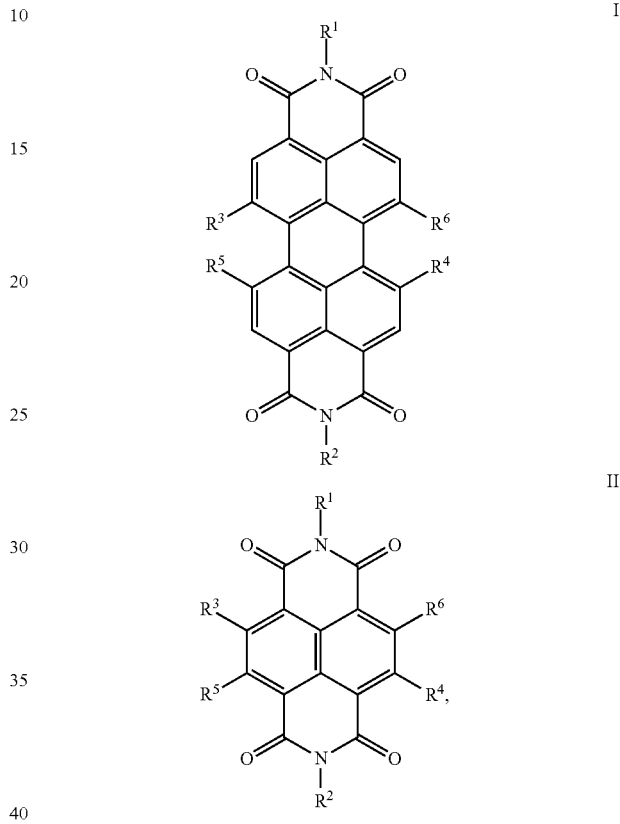

wherein:
$R^1$ and $R^2$, at each occurrence, independently are selected from the group consisting of a $C_{1-30}$ alkyl group, a $C_{2-30}$ alkenyl group, a $C_{2-30}$ alkynyl group, and a $C_{1-30}$ haloalkyl group,
$R^3$, $R^4$, $R^5$, and $R^6$ independently are H or an electron-withdrawing group, wherein at least one of $R^3$, $R^4$, $R^5$, and $R^6$ is an electron-withdrawing group; and
a non-conductive polymer,
wherein the non-conductive polymer is poly(methylmethacrylate), and
wherein a weight ratio of the compound of the formula I or II to the non-conductive polymer in the thin film semiconductor is from 5:1 to 1:5.

2. The thin film semiconductor of claim 1, wherein $R^1$ and $R^2$, at each occurrence, are selected from the group consisting of a $C_{1-12}$ alkyl group and a $C_{1-12}$ haloalkyl group.

3. The thin film semiconductor of claim 1, wherein each of $R^3$, $R^4$, $R^5$, and $R^6$ is selected from the group consisting of H, F, Cl, Br, I, and —CN.

4. The thin film semiconductor of claim 1, wherein each of $R^3$ and $R^4$ is Br or CN and $R^5$ and $R^6$ are H.

5. The thin film semiconductor of claim 1, wherein each of $R^3$ and $R^6$ is Br or —CN and $R^4$ and $R^5$ are H.

6. The thin film semiconductor of claim 1, wherein the compound has the following formula Ia or formula Ib:

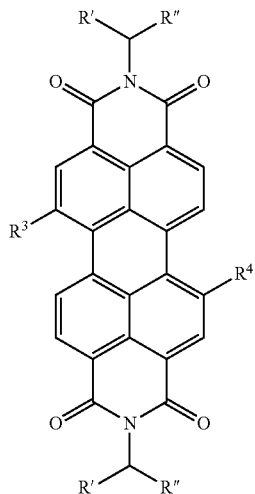

Ia

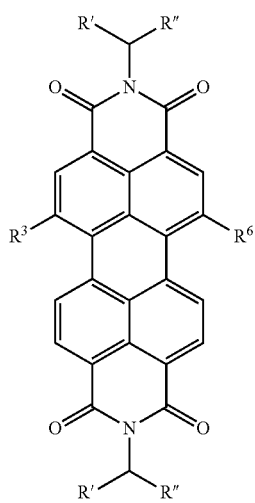

Ib wherein R', R" are, at each occurrence, selected from the group consisting of a $C_{1-12}$ alkyl group and a $C_{1-12}$ haloalkyl group, and $R^3$, $R^4$, and $R^6$ are as defined in claim 1.

7. The thin film semiconductor of claim 1, wherein the compound of the formula I is

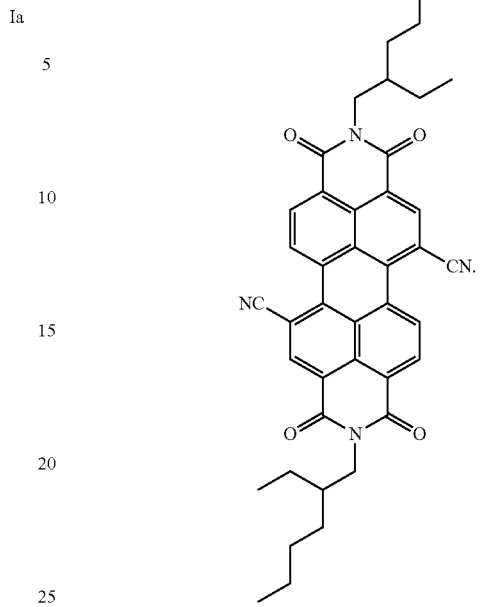

8. The thin film semiconductor of claim 1, wherein the compound of formula II is

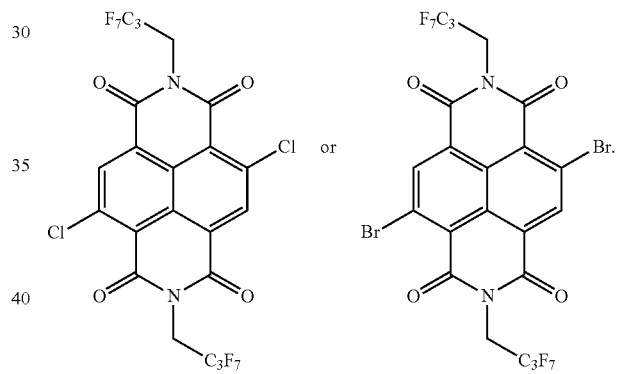

9. A solution comprising at least one compound of the following formula I or II:

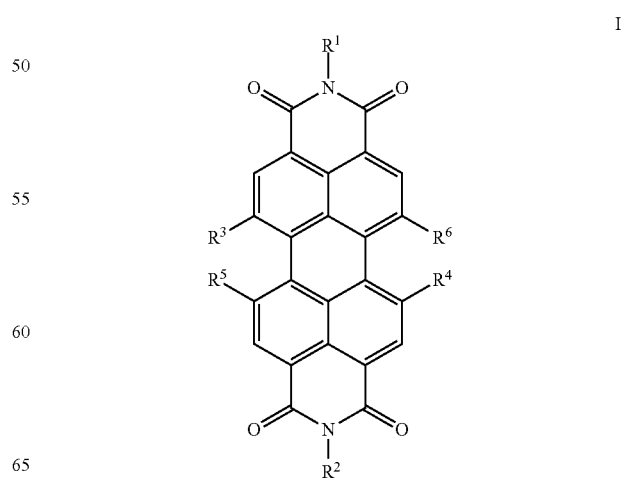

I

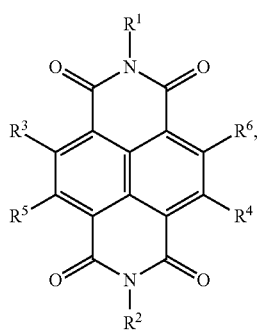

wherein:
$R^1$ and $R^2$ each independently, are selected from the group consisting of a $C_{1-30}$ alkyl group, a $C_{2-30}$ alkenyl group, a $C_{2-30}$ alkynyl group, and a $C_{1-30}$ haloalkyl group,
$R^3$, $R^4$, $R^5$, and $R^6$ each independently, are H or an electron-withdrawing group, wherein at least one of $R^3$, $R^4$, $R^5$, and $R^6$ is an electron-withdrawing group,
a non-conductive organic polymer, and
a solvent,
wherein the non-conductive organic polymer is poly(methylmethacrylate), and
wherein a weight ratio of the compound of the formula I or II to the non-conductive organic polymer in the solution is from 5:1 to 1:5.

* * * * *